United States Patent
Gonzalez-Hernandez

(10) Patent No.: US 8,900,302 B2
(45) Date of Patent: Dec. 2, 2014

(54) TENDON CRIMP FOR PASSAGE INTO A BONE TUNNEL AND METHOD FOR USE THEREOF

(75) Inventor: Eduardo Gonzalez-Hernandez, Coconut Grove, FL (US)

(73) Assignee: Toby Orthopaedics, Inc., Miami, FL (US)

(*) Notice: Subject to any disclaimer, the term of this patent is extended or adjusted under 35 U.S.C. 154(b) by 0 days.

(21) Appl. No.: 13/601,282

(22) Filed: Aug. 31, 2012

(65) Prior Publication Data

US 2013/0060333 A1    Mar. 7, 2013

Related U.S. Application Data

(60) Provisional application No. 61/529,994, filed on Sep. 1, 2011.

(51) Int. Cl.
 *A61F 2/08* (2006.01)

(52) U.S. Cl.
 USPC ........................................................ 623/13.15

(58) Field of Classification Search
 USPC ............................................. 623/13.11–13.2
 See application file for complete search history.

(56) References Cited

U.S. PATENT DOCUMENTS

| | | | |
|---|---|---|---|
| 3,620,218 A | 11/1971 | Schmitt et al. | |
| 3,842,441 A | 10/1974 | Kaiser | |
| 4,584,722 A | 4/1986 | Levy et al. | |
| 4,733,850 A | 3/1988 | Thompson | |
| 4,781,191 A | 11/1988 | Thompson | |
| 5,431,153 A | 7/1995 | Lee | |
| 5,456,721 A * | 10/1995 | Legrand | 623/13.15 |
| 5,531,232 A | 7/1996 | Hill | |
| 5,651,790 A | 7/1997 | Resnick et al. | |
| 5,803,904 A | 9/1998 | Mehdizadeh | |
| 5,893,861 A | 4/1999 | Yumoto | |
| 5,897,591 A | 4/1999 | Kobayashi | |
| 6,033,361 A | 3/2000 | Co et al. | |
| 6,056,762 A | 5/2000 | Nash et al. | |
| 6,080,192 A * | 6/2000 | Demopulos et al. | 623/13.14 |
| 6,083,244 A | 7/2000 | Lubbers et al. | |
| 6,743,243 B1 | 6/2004 | Roy et al. | |
| 6,984,241 B2 | 1/2006 | Lubbers et al. | |
| 7,112,221 B2 | 9/2006 | Harris | |
| 7,144,424 B2 | 12/2006 | Steenlage | |

(Continued)

FOREIGN PATENT DOCUMENTS

| | | |
|---|---|---|
| EP | 1 757 231 A1 | 2/2007 |
| GB | 2 424 372 A | 9/2006 |

(Continued)

OTHER PUBLICATIONS

Biologically Oriented Prostheses (BIOPRO); Tendone!® product brochure; 2 pages.

(Continued)

*Primary Examiner* — Alvin Stewart
(74) *Attorney, Agent, or Firm* — Martin & Ferraro, LLP

(57) ABSTRACT

A surgical device and method is used in attaching a tendon or a ligament to bone. In a preferred form, the device is a crimp configured to reduce the thickness of the free end of the tendon or the ligament to facilitate insertion of the tendon or the ligament into an opening formed in the bone.

14 Claims, 7 Drawing Sheets

(56) References Cited

U.S. PATENT DOCUMENTS

| | | |
|---|---|---|
| 8,075,575 B2 | 12/2011 | Gonzalez-Hernandez |
| 8,454,628 B2 * | 6/2013 | Smith et al. .................. 606/139 |
| 2004/0230223 A1 * | 11/2004 | Bonutti et al. ................. 606/232 |
| 2004/0236374 A1 * | 11/2004 | Bonutti et al. ................. 606/232 |
| 2005/0033338 A1 | 2/2005 | Ferree |
| 2005/0159812 A1 | 7/2005 | Dinger III et al. |
| 2005/0203620 A1 | 9/2005 | Steiner et al. |
| 2005/0228426 A1 | 10/2005 | Campbell |
| 2005/0245958 A1 | 11/2005 | Carlson et al. |
| 2006/0041270 A1 | 2/2006 | Lenker et al. |
| 2007/0162022 A1 | 7/2007 | Zhang et al. |
| 2007/0288043 A1 | 12/2007 | Rehnke |
| 2008/0039873 A1 * | 2/2008 | Bonutti et al. ................. 606/139 |
| 2008/0109021 A1 | 5/2008 | Medoff |
| 2009/0048616 A1 | 2/2009 | Gonzalez-Hernandez |
| 2010/0137883 A1 | 6/2010 | Gonzalez-Hernandez |
| 2010/0145448 A1 * | 6/2010 | Montes De Oca Balderas et al. ................. 623/13.14 |
| 2011/0015656 A1 | 1/2011 | Gonzalez-Hernandez |
| 2011/0087248 A1 | 4/2011 | Steffen |
| 2011/0112532 A1 | 5/2011 | Steffen |
| 2012/0071975 A1 | 3/2012 | Gonzalez-Hernandez |
| 2012/0078283 A1 | 3/2012 | Gonzalez-Hernandez |
| 2012/0083848 A1 | 4/2012 | Gonzalez-Hernandez |
| 2013/0060333 A1 * | 3/2013 | Gonzalez-Hernandez 623/13.15 |

FOREIGN PATENT DOCUMENTS

| | | |
|---|---|---|
| JP | HEI 09-75362 | 9/1997 |
| WO | WO 2006/085090 A2 | 8/2006 |
| WO | WO 2008/017834 | 2/2008 |

OTHER PUBLICATIONS

Kamath, B. Jagannath, et al.; Technique Article; A Simple, Semirigid, and Surgeon-Friendly Tendon Retriever and Flexor Sheath Dilator; The Journal of Hand Surgery, vol. 32A, No. 2, Feb. 2007, pp. 269-273.

Sourmelis, S.G., et al.; Retrieval of the Retracted Flexor Tendon; Journal of Hand Surgery (British and European Volume), vol. 12-B, No. 1, Feb. 1987, cover page and pp. 109-111.

Supplementary Partial European Search Report; Application No. EP 08 82 7278; mailed Jun. 30, 2011; 6 pages.

* cited by examiner

TENDON CRIMP FOR PASSAGE INTO A BONE TUNNEL AND METHOD FOR USE THEREOF

CROSS-REFERENCE TO RELATED APPLICATIONS

This application claims the benefit of U.S. Provisional Application No. 61/529,994, filed September 1, 2011, entitled "Tendon Crimp For Passage into Bone Tunnel," which is incorporated by reference herein.

FIELD OF THE INVENTION

The present invention relates to improvements in the attachment of tissue structures to bone.

BACKGROUND OF THE INVENTION

In orthopaedic surgery there are many procedures that make use of a tendon or a ligament graft which is tunnelled into a bone tunnel. The goal is to reconstruct a ligament where no other option may work and where the surgeon needs to recreate a strong ligament/tendon interface as part of a procedure.

As shown in FIG. 1, those familiar in the art of orthopaedic surgery know that the task of passing a tendon or a ligament graft 10 into a bone 20 having a bone tunnel 30 can be a very frustrating experience. In most instances the graft to be tunnelized sustains significant damage in the process. It is often desirable to pass the thickest graft possible through the smallest tunnel, but even passage of a graft through a bone tunnel that is near equal in size is simply not practical and the surgeon has to settle for passing a significantly smaller graft through a larger tunnel to avoid the complications of the process.

The present invention seeks to lessen these problems by providing a device and method which allows a tissue structure such as a tendon or a ligament to be inserted into a bone tunnel without many of the disadvantages of conventional devices and methods.

SUMMARY

The device in one or more embodiments of the present invention includes a crimp that acts on the free end of the graft, usually a tendon or a ligament, to be inserted into the tunnel. Unless otherwise indicated, the present invention will be described for use with a tendon, though it will be appreciated that the invention is not so limited. For example, preferred embodiments of the present invention may be configured for use with other tissue structures or grafts such as ligaments. A crimper is utilized to compress the crimp in place. The crimp is applied to the free end of the tendon to compress the tendon and squeeze the fluid content and reduce the segment of tendon under the crimp. The leading end of the tendon is now optimized for passage into a bone tunnel.

The present invention in one preferred aspect provides for a method for inserting a free end of a tendon or a ligament into a bone. The method includes forming an opening in the bone; crimping a portion of the free end of the tendon or the ligament with a crimp; and inserting at least the crimped portion of the tendon or the ligament into the opening of the bone.

In another preferred aspect, the present invention provides for a method for inserting a free end of a tendon or a ligament into a bone. The method includes: forming an opening in the bone; enclosing a portion of the free end of the tendon or the ligament with a sleeve having a central longitudinal axis and a minimum cross-section perpendicular to the central longitudinal axis, the sleeve being biodegradable; reducing the minimum cross-section of the sleeve to crimp the portion of the free end of the tendon or the ligament; inserting the crimped portion of the tendon or the ligament into the opening of the bone; and permitting the sleeve to biodegrade so that the crimped portion of the tendon or the ligament expands within the opening.

In a further preferred aspect, the present invention provides for a surgical kit for attaching a tendon or a ligament to bone. The kit includes a crimp composed of a surgical grade material, the crimp having an interior surface and an exterior surface, the interior and exterior surfaces each having a plurality of surface projections. The kit also includes an insertion shield for placement in front of the crimp when the crimp is engaged with the tendon or the ligament, the insertion shield being configured to facilitate insertion of the crimp into an opening in the bone, the insertion shield having an insertion end, a trailing end, a length from the insertion end to the trailing end, a central longitudinal axis and a minimum cross-section perpendicular to the central longitudinal axis, the minimum cross-section decreasing along at least a portion of the length towards the leading end.

In yet a further aspect, the present invention provides for a sleeve for attaching a free end of tendon or ligament to bone. The sleeve includes a body having a first end, a second end, a length from the first end to the second end and a circumferential wall from the first end to the second end, the wall forming a passage from the first end to the second end, the passage having a central longitudinal axis and a minimum cross-section perpendicular to the central longitudinal axis. The sleeve includes a plurality of openings in the wall. The body of the sleeve is formed of a biodegradable material. The body of the sleeve is configured to reduce from a first minimum cross-section in which the free end of the tendon or the ligament may be inserted into the passage to a second minimum cross-section which traps at last a portion of the free end of the tendon or the ligament in the passage.

It is to be understood that both the foregoing general description and the following detailed description are exemplary and explanatory only and are not restrictive of the invention, as claimed.

The accompanying drawings, which are incorporated in and constitute a part of this specification, illustrate several embodiments of the invention and together with the description, serve to explain the principles of the invention.

DETAILED DESCRIPTION OF THE DRAWINGS

Figure 1:
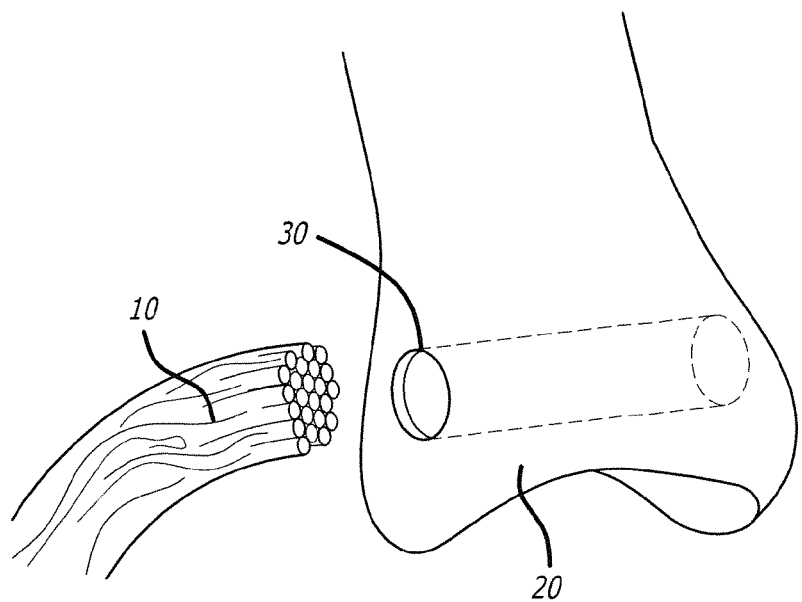
FIG. 1 is a partial perspective view of a tendon and an end of a bone with a bone tunnel shown in hidden outline.

Reference will now be made in detail to the present preferred embodiments of the invention, examples of which are illustrated in the accompanying drawings.

FIGS. 2 to 5 show a preferred embodiment of a crimp 100, an insertion shield 102 and a suture 104 for engagement with a portion of a free end 12 of tendon 10. In use, crimp 100 is crimped around a portion of suture 104 and free end 12 of tendon 10. Insertion shield 102 is slid along suture 104 until it abuts free end 12 of tendon 10. Free end 12 of tendon 10 is then pulled into the bone tunnel together with the assembly of crimp 100 and insertion shield 102 using suture 104. The preferred elements of the device and their interrelationship are described below.

Figure 2:
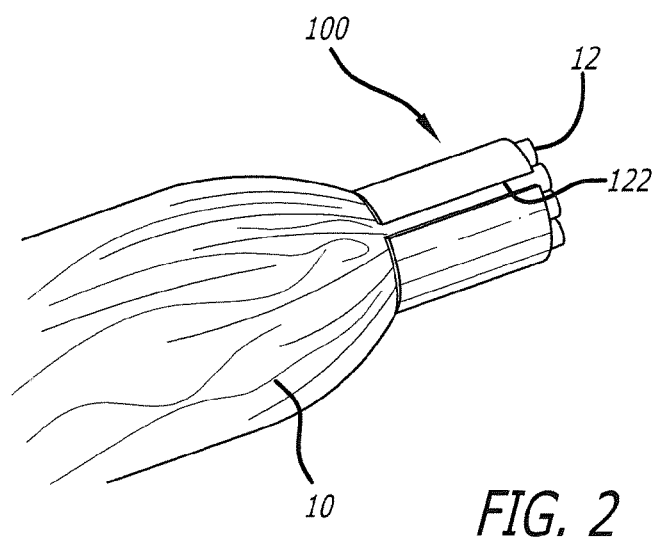
FIG. 2 is a partial perspective view of a crimp in accordance with a preferred embodiment of the present invention shown crimping a portion of the free end of a tendon.
Figure 3:
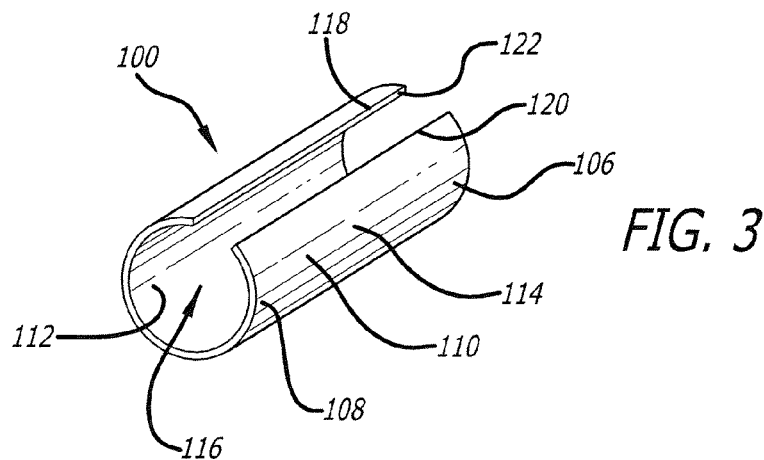
FIG. 3 is a perspective view of the crimp of FIG. 2.

Referring to FIGS. 2 and 3, crimp 100 has a first end 106, a second end 108, a circumferential wall 110, an interior surface 112 and an exterior surface 114. Interior surface 112 of wall 110 forms a passage 116 from first end 106 to second end 108. Wall 110 preferably has a pair of longitudinal edges 118, 120 that form a slit or slot 122. While in an uncontracted state, passage 116 is preferably sized and configured to accommodate the insertion of the free end of the tendon therein. After the tendon has been inserted at least part way into passage 116, crimp 100 is crimped, reducing the minimum cross-section of passage 116 and compressing the tendon within crimp 100 as shown in FIG. 2.

Crimp 100 is preferably formed from a surgical grade material that is configured to be bent or crimped, preferably with a crimper. Examples of materials suitable for use with crimp 100 include, but are not limited to, metals such as titanium, stainless steel, and nitinol, and various non-metal materials and polymers.

Figure 4:
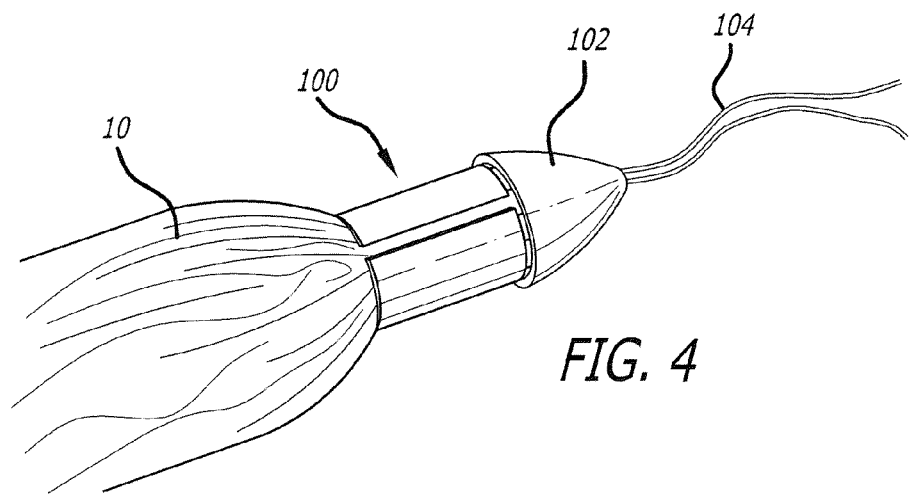
FIG. 4 is a partial perspective view of the crimp of FIG. 3 shown engaged with the tendon, together with an insertion shield for facilitating insertion of the crimp, and a suture for pulling the crimp and insertion shield through an opening in the bone.
Figure 5:
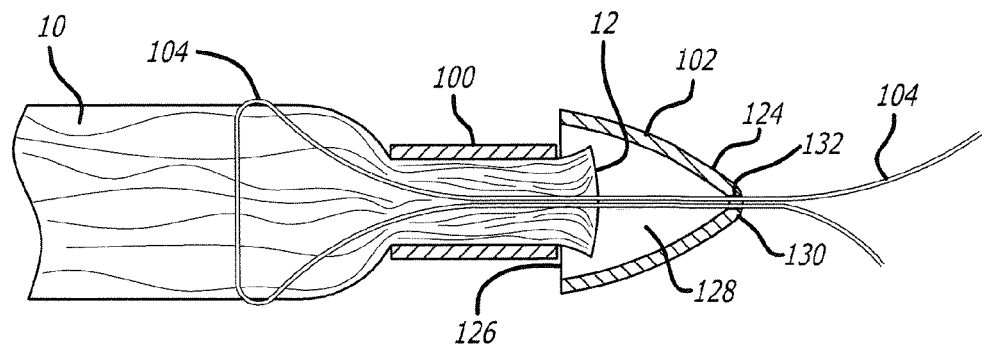
FIG. 5 is a partial cross-sectional side view of the crimp, insertion shield and suture of FIG. 4.

A shown in FIGS. 4 and 5, insertion shield 102 includes an insertion end 124, a trailing end 126, an interior 128, and a preferably frusto-conical, bullet-like tip 130 for smoother passage through the bone tunnel. Tip 130 preferably includes an aperture 132 sized and configured for the passage of suture 104 therethrough. In use, suture 104 can be placed into tendon 10 prior to the application of crimp 100. Suture 104 passes through aperture 132 and the center of bullet tip 130. A pull on suture will 104 provide the necessary traction to deliver the assembly through the bone tunnel. Insertion shield 102 preferably facilitates the insertion of the free end of the tendon into the bone tunnel by providing a ramped surface to minimize interference between the free end of the tendon and the bone tunnel during insertion of the free end into the bone tunnel. The interaction between insertion shield 102, crimp 100 and suture 104 will be described in further detail below in relation to a preferred method in accordance with another preferred embodiment of the present invention.

Figure 6:
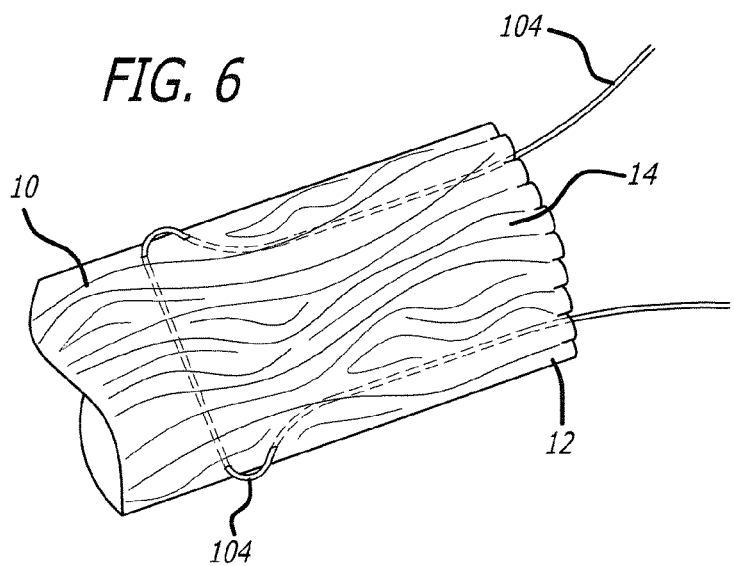
FIG. 6 is a partial side elevation view showing the engagement of the suture with the free end of the tendon in accordance with a preferred method of the present invention.
Figure 7:
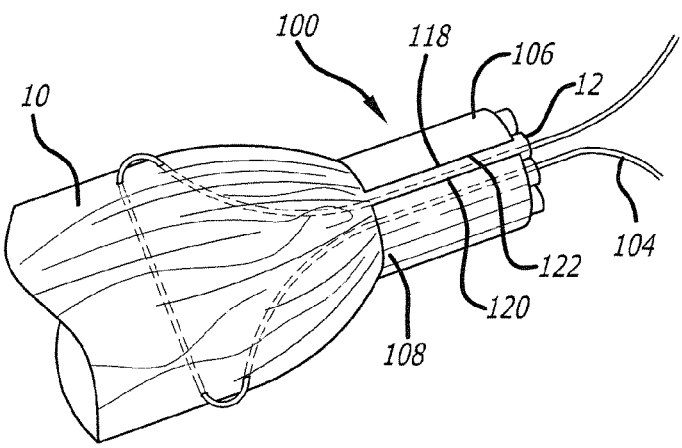
FIG. 7 is a partial perspective view of the crimp of FIG. 3 shown crimping a portion of the free end of the tendon in accordance with a preferred method of the present invention.

Having described the preferred components of the device, a preferred method of use will now be described with reference to FIGS. 6 to 11. Referring to FIG. 6, suture 104 is inserted into free end 12 of tendon 10, preferably by looping the suture through and around fibers 14 of tendon 10. As shown in FIG. 7, crimp 100 is placed around a portion of free end 12, and then crimped. The free end of tendon 10 may be inserted into second end 108 and through passage 116 of crimp 100. Alternatively, slit 122 may have a distance between longitudinal edges 118, 120 sufficient to permit the thickness of tendon 10 therethrough so that the tendon is inserted into passage 116 laterally through slit 122. Once tendon 10 is in passage 116, crimp 100 is preferably crimped using a crimper. The crimping of crimp 100 preferably compresses free end 12 of tendon 10, squeezing the fluid content from the portion being crimped and reducing the thickness of free end 12. The compression also enhances the securing of suture 104 to free end 12 of tendon 10.

Figure 8:
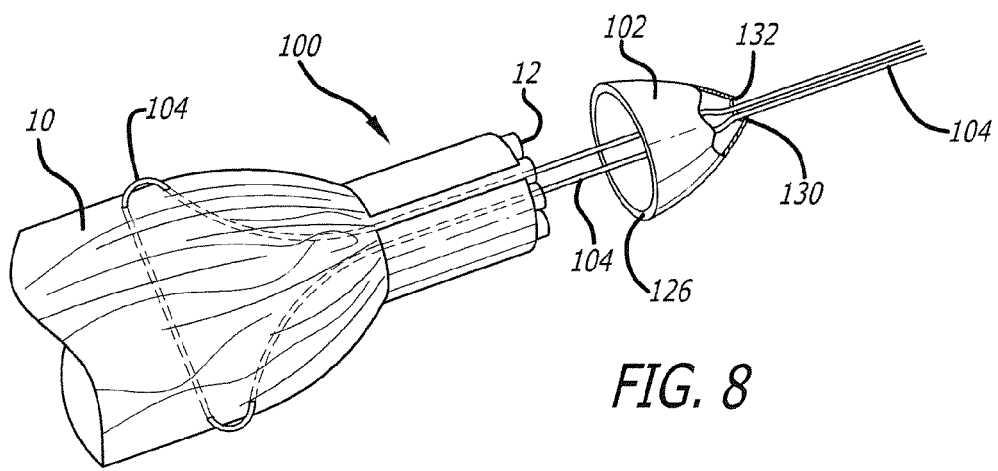
FIG. 8 is a partial perspective view of the insertion shield of FIG. 4 shown being inserted along the suture in accordance with a preferred method of the present invention.

FIG. 8 shows the engagement of insertion shield 102 with suture 104 and crimp 100. The ends of suture 104 are inserted through trailing end 126 and aperture 132 of insertion shield 102. Insertion shield 102 is moved toward free end 12 of tendon 10 until it preferably comes into contact with free end 12 and/or crimp 100. Preferably at least a portion of free end 12, more preferably a portion of free end 12 and crimp 100 are inserted into trailing end 126 of insertion shield 102.

Figure 9:
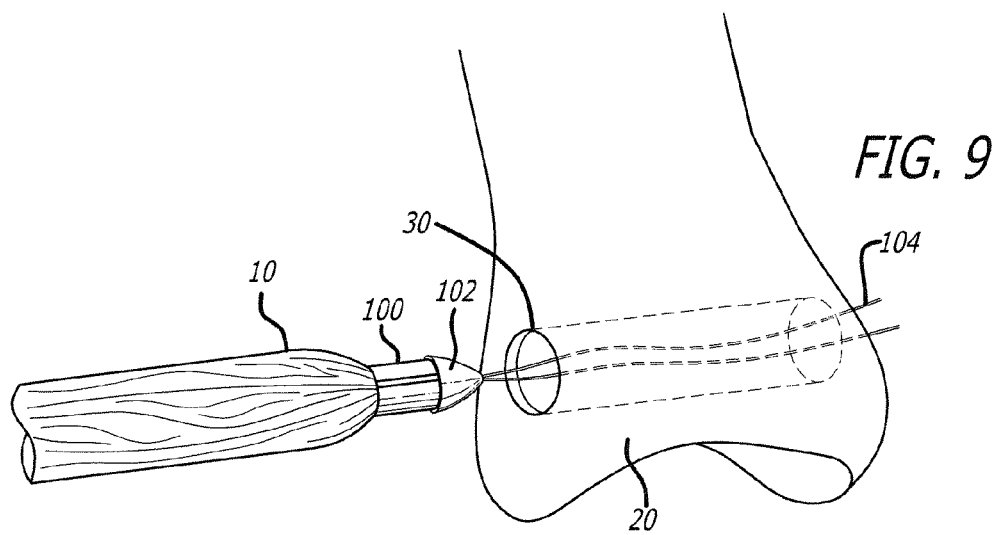
FIG. 9 is a partial perspective view of the suture of FIG. 8 shown inserted through a tunnel in an end of a bone in accordance with a preferred method of the present invention.
Figure 10:
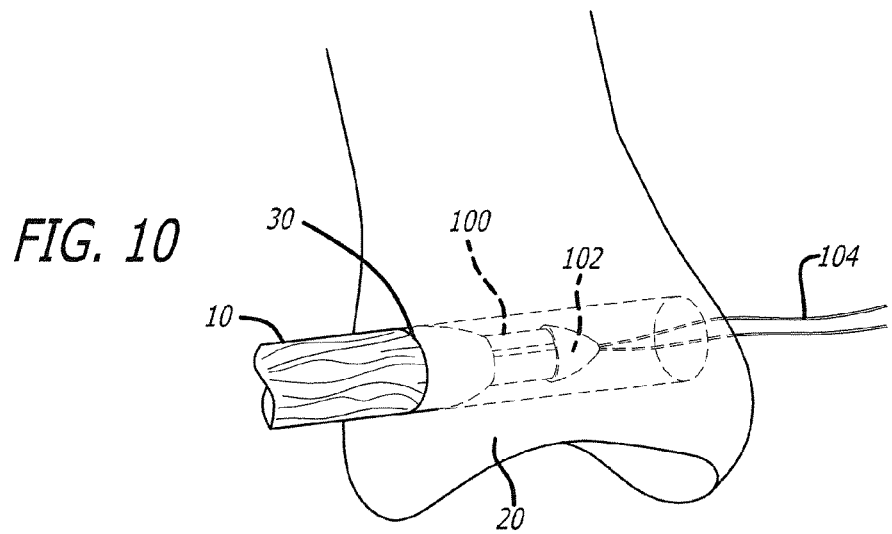
FIG. 10 is a partial perspective view of the crimp and insertion shield of FIG. 4 shown pulled partially inside the tunnel in accordance with a preferred method of the present invention.
Figure 11:
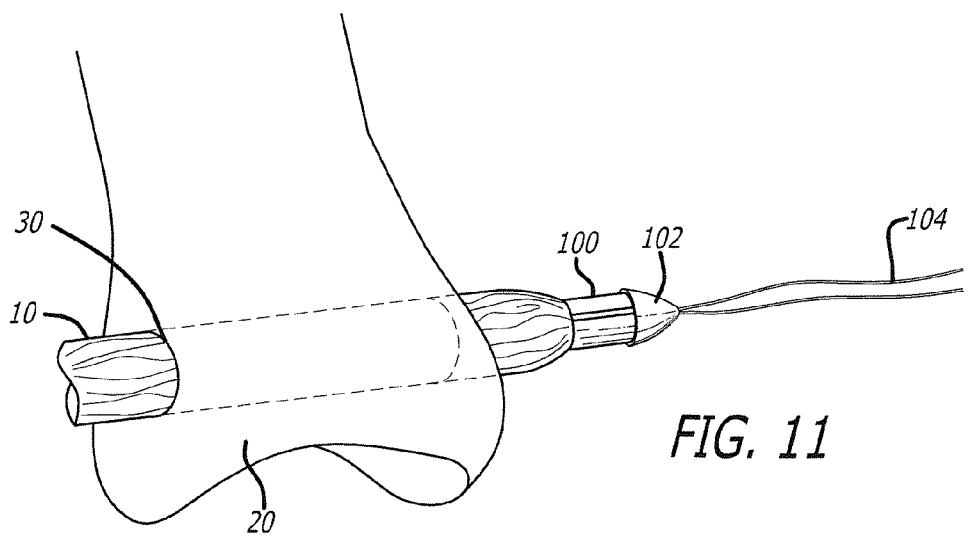
FIG. 11 is a partial perspective view of the crimp and insertion shield of FIG. 4 shown pulled through the tunnel in accordance with a preferred method of the present invention.

Referring to FIG. 9, an opening is formed into a portion of bone 20. The opening is preferably formed as a through-hole or bone tunnel 30. The ends of suture 104 are inserted into and through bone tunnel 30 until they exit the opposite end of the tunnel. Suture 104 is moved to pull insertion shield 102, crimp 100 and free end 12 of tendon 10 at least partially into bone tunnel 30 as shown in FIG. 10. Referring to FIG. 11, continued pulling on suture 104 moves the free end of tendon 10 out the other side of bone tunnel 30, where the crimped portion of the free end may be severed if desired.

It will be appreciated that the steps described above may be performed in a different order, varied, or certain steps added or omitted entirely without departing from the scope of the present invention. For example only, instead of moving the crimped portion of free end 12 of tendon 10 completely through the bone tunnel, the crimped portion may be left in the bone tunnel.

FIGS. 12 to 18 show additional preferred embodiments of the present invention. Unless otherwise noted, the description of crimp 100 above will be understood to apply to the embodiments in FIGS. 12 to 18 as appropriate.

Figure 12:
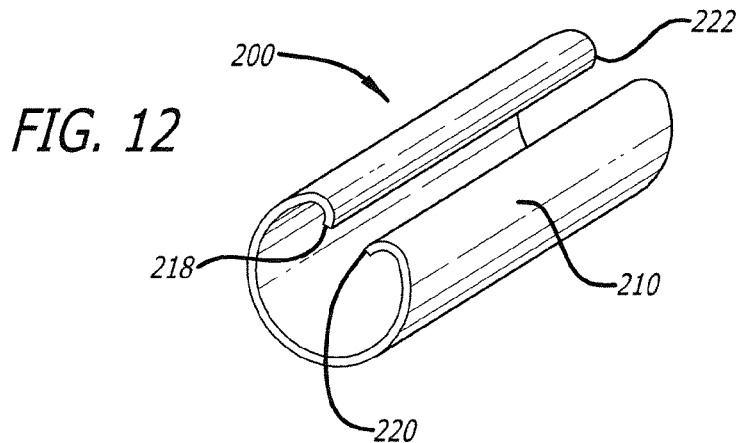
FIG. 12 is a perspective view of a crimp in accordance with another preferred embodiment of the present invention.
Figure 13:
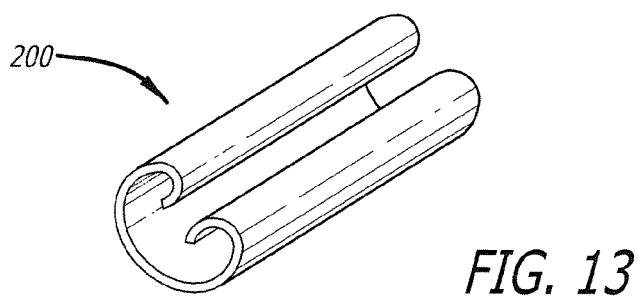
FIG. 13 is a perspective view of the crimp of FIG. 12 shown partially crimped.

Referring now to FIGS. 12 and 13, a crimp 200 is shown in accordance with another preferred embodiment of the present invention. Crimp 200 is similar to crimp 100 except that wall 210 of crimp 200 forms a more complex cylindrical form with curved longitudinal surfaces 218, 220 adjacent longitudinal slit 222 creating a double barrel crimp form for additional strength and hold on the tendon. FIG. 12 shows crimp 200 in a non-compressed state. FIG. 13 shows crimp 200 in a compressed state.

Figure 14:
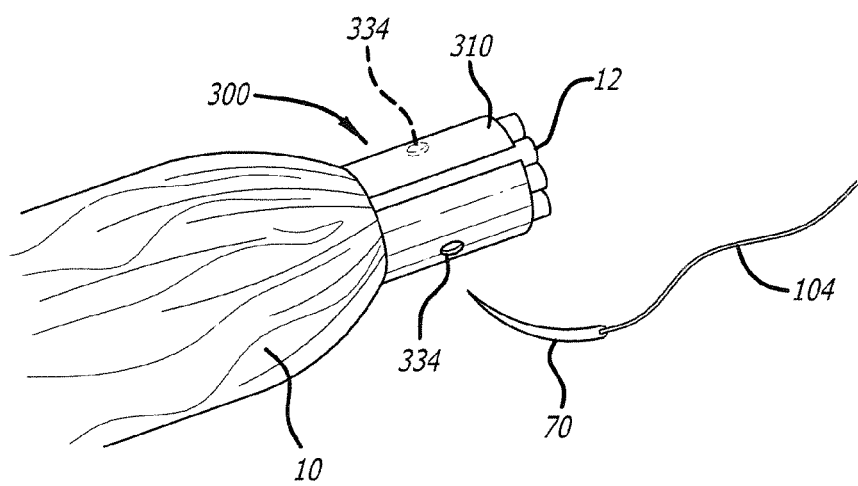
FIG. 14 is a partial perspective view of a crimp in accordance with a further preferred embodiment of the present invention shown crimping a portion of the free end of a tendon.

Referring now to FIG. 14, a crimp 300 is shown in accordance with another preferred embodiment of the present invention. Crimp 300 is similar to crimp 100 except that wall 310 of crimp 300 preferably includes a pair of orifices or apertures 334 therethrough. Apertures 334 are preferably oriented so that when crimp 300 is compressed, apertures 334 are opposite one another along an axis. As shown in FIG. 14, crimp 300 may be applied to free end 12 of tendon 10 before inserting the suture. Once crimp 300 is applied to free end 12, a curved needle 70 attached to an end of the suture may be inserted through one of apertures 334, through tendon 10, and out the other of apertures 334. Thereafter, free end 12 may be pulled through the bone tunnel in a manner similar to that described above with respect to crimp 100.

Figure 15:
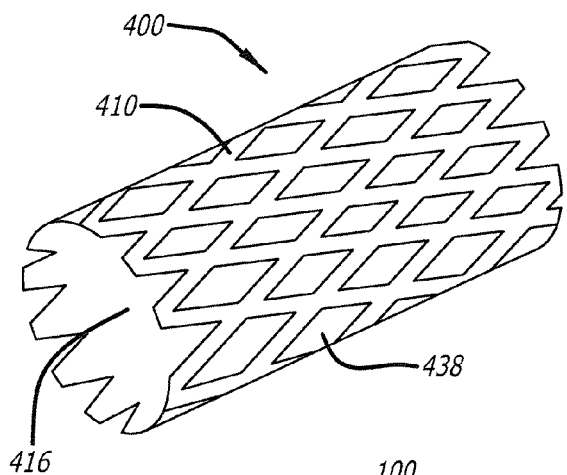
FIG. 15 is a perspective view of a crimp in accordance with an additional preferred embodiment of the present invention.

Referring now to FIG. 15, a crimp 400 is shown in accordance with another preferred embodiment of the present invention. As shown in FIG. 15, crimp 400 may be formed as a compressible stent-like sleeve. Wall 410 of crimp 400 preferably has a circumferential lattice structure with a plurality of openings 438. In use, the free end of the tendon is placed into passage 416 of crimp 400. Thereafter, crimp 400 is crimped to reduce the minimum cross-section of the crimp and at least a portion of the free end of the tendon.

It will be appreciated that the minimum cross-section of crimp 400 may be reduced non-mechanically. For example only, crimp 400 may be made of a shape material such as nitinol that is programmed to contract or expand at a preset temperature. Crimp 400 may be formed from a non-metallic material or biomaterial, such as a biodegradable or bioresorbable material. The composition of such materials will be well-understood by those of ordinary skill in the art. When formed from a non-metallic or biomaterial, wall 410 may be configured to cinch around at least a portion of the free end of the tendon to trap the portion therein. A projection or thread may extend from one of the ends of the wall to facilitate pulling of the crimp through the opening in the bone.

Figure 16:
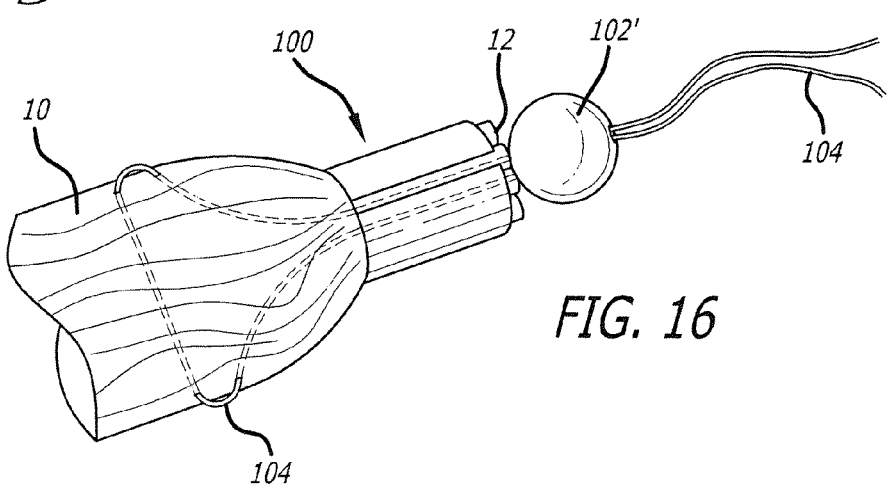
FIG. 16 is a partial perspective view of the crimp of FIG. 3 with a spherical insertion shield in accordance with another preferred embodiment of the invention.

Referring now to FIG. 16, an insertion shield 102' is shown in accordance with another preferred embodiment of the present invention. Insertion shield 102' is similar to insertion shield 102 except that it is spherically-shaped to facilitate insertion of crimp 100 and free end 12 of tendon 10 through the bone tunnel. The insertion shield may also be formed as other shapes, for example only, an ovoid or ellipsoid. The insertion shield may be formed as a separate component relative to the crimp, or may be formed as an integral part of the crimp, as described in further detail below. Suture 104 may be applied to tendon 10 prior to the application of the crimper, and then through insertion shield 102'.

Figure 17:
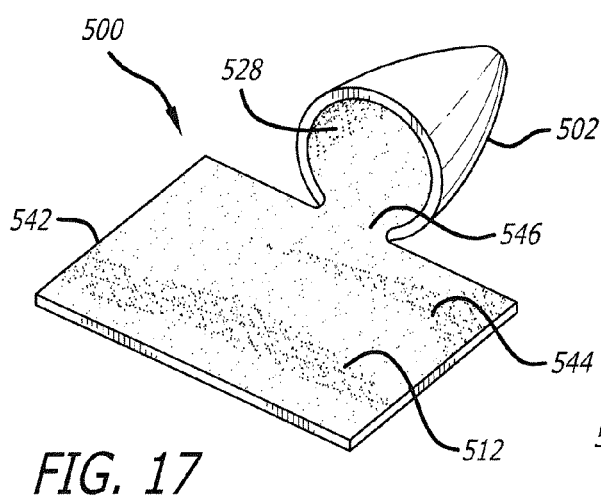
FIG. 17 is a perspective view of a crimp in accordance with another preferred embodiment of the present invention.
Figure 18:
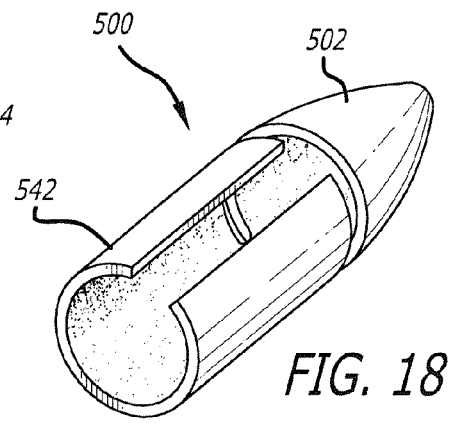
FIG. 18 is a perspective view of the crimp of FIG. 17 shown partially crimped.

Referring now to FIGS. 17 and 18, a crimp 500 is shown in accordance with another preferred embodiment of the present invention. Crimp 500 is similar to crimp 100 except that insertion shield 502 is integrally formed with a main body portion 542 of crimp 500. Body portion 542 has an interior surface 512 that preferably includes a plurality of surface roughenings 544 configured to enhance the securing of crimp 500 to the free end of the tendon. Insertion shield 502 and body portion 542 are connected to one another by a neck 546. As shown in FIG. 17, insertion shield 502 is preferably formed in a frusto-conical bullet-nose configuration while body portion 542 is preferably initially planar or at least not entirely circular in a cross-section transverse to the longitudinal axis of the crimp. Crimp 500 may be applied by inserting the distal-most portion of the free end of the tendon into interior 528 of insertion shield 502, then crimping body portion 542 around another portion of the free end of the tendon. Preferably, when body portion 542 is crimped, it will have an interior cross-section approximately equally to the maximum interior cross-section of insertion shield 502.

Figure 19:
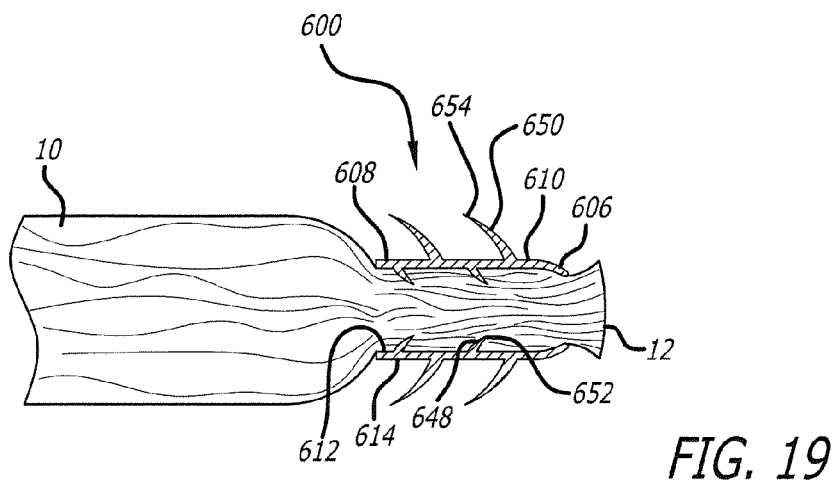
FIG. 19 is a partial cross-sectional side view of a crimp in accordance with another preferred embodiment of the present invention.
Figure 20:
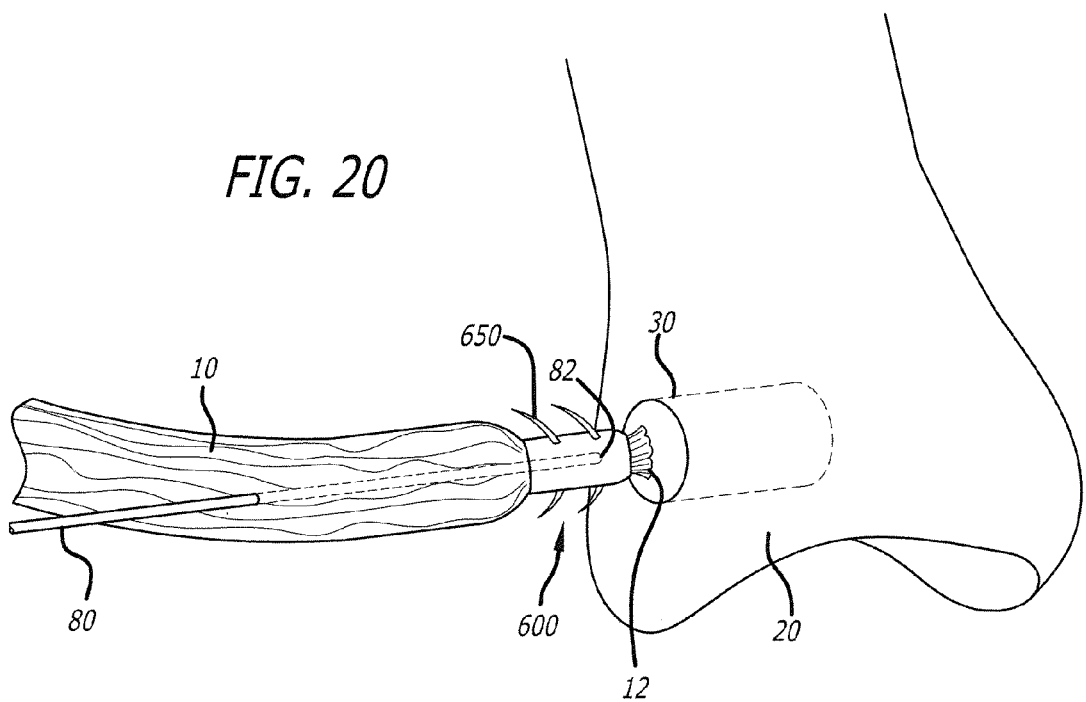
FIG. 20 is a partial perspective view of the crimp of FIG. 19 being inserted into an opening in bone in accordance with another preferred method of the present invention.

Referring now to FIGS. 19 and 20, a crimp 600 is shown in accordance with another preferred embodiment of the present invention. Crimp 600 is similar to crimp 100 except that it includes a plurality of surface projections preferably formed as flexible spines, quills or fingers. In particular, wall 610 of crimp 600 has an interior surface 612 with a plurality of interior spines 648, and an exterior surface 614 with a plurality of exterior spines 650. As shown in FIG. 19, interior spines 648 each include a tip 652 that is preferably oriented toward first end 606 of crimp 600. Interior spines 648 are preferably resilient and flexible so as to facilitate insertion of free end 12 of the end of tendon 10 into crimp 600, while resisting expulsion of free end 12 therefrom.

Exterior spines 650 each include a tip 654 preferably oriented toward second end 608 of crimp 600. Exterior spines 650 are preferably resilient and flexible so as to facilitate insertion of crimp 600 into the opening in the bone, while resisting expulsion of crimp 600 therefrom. The lengths of interior spines 648 and exterior spines 650 may be different compared to one another. For example, as shown in FIG. 19, the length of each interior spine 648 is preferably shorter than the length of each exterior spine 650. The length of each interior spine 648 is preferably less than or equal to one-half the maximum inner dimension that is perpendicular to the length of crimp 600. The length of each exterior spine 650 is preferably equal to or greater than one-half the maximum inner dimension that is perpendicular to the length of crimp 600.

Referring now to FIG. 20, crimp 600 is preferably inserted into opening 30 of bone 20 using a push-rod 80. Once free end 12 of tendon 10 is placed into crimp 600, leading end 82 of push-rod 80 is inserted through fibers 14 of tendon 10 and preferably into the interior of crimp 600. The surgeon may guide crimp 600 into opening 30 using push-rod 80 as shown in FIG. 20. After inserting crimp 600 into opening 30, push-rod 80 is disengaged from tendon 10.

The foregoing description is by way of example only, and may be varied considerably without departing from the scope of the present invention. For example only, the crimp may be applied without a suture. In particular, the crimp may have a leading suture or wire already attached to it so that upon its application on the leading free end of the tendon graft, the assembly is ready for passage through the bone tunnel without having to apply a suture. Alternatively, the crimp may be pushed into the bone using, for example, a push-rod as described above.

The crimp may be configured for use without an insertion shield. For example only, the crimp may have a preconfigured, at least partially frusta-conical shape so that when crimped around the free end of the tendon, the crimp will have a taper adapted to facilitate insertion of the tendon into the bone tunnel.

The crimp may have a thickness that varies along its length. For example only, the exterior may have a preconfigured, at least partially frusto-conical shape while the interior of the crimp may be configured with a generally uniform passage, for example, a cylindrical passage.

Instead of, or in addition to the crimp having an at least partially frusto-conical shape, the crimping tool may be configured with a plate or plates that have an at least partially frusto-conical shape. For example only, a crimping tool with two at least partially frusto-conical plates may be configured to crimp the crimp so that the crimp is tapered from its trailing end towards its leading end. Such a configuration would reduce the need for an insertion shield.

The exterior surface of the crimp may include surface roughenings or projections 650. The surface roughenings or projections 650 may be configured to facilitate insertion while resisting expulsion of the crimp from the opening in the bone, such as shown in FIGS. 19 and 20. The surface roughenings 650 may be configured, for example only, as a textured or etched surface or a pattern of dimples and/or grooves. Examples of surface projections 650 include ratchetings, or as shown in FIGS. 19 and 20 spines, quills and/or fingers, which may be configured for one way insertion if desired. As shown in FIGS. 19 and 20 exterior projections 650 extend in a generally arcuate configuration from the exterior wall of crimp 600 in a direction extending from end 606 toward end 608. Moreover, as shown in FIG. 19, exterior projections 650 are integral with, and made of the same material as, the crimp 600.

The interior surface of the crimp may include surface roughenings or projections 648 to enhance the securing of the crimp to the tendon. The crimp may include surface roughenings or projections only on its interior surface, only on its exterior surface, or on both the interior and exterior surfaces. Where both the interior and exterior surfaces include surface roughenings or projections, such surface roughenings or projections may be differently configured. For example only, the interior surface may include surface roughenings, or a plurality of ratchets, while the exterior surface may include a plurality of one-way ratchets. As shown in FIGS. 19 and 20 interior projections 648 extend from the interior wall of crimp 600 in a direction extending from end 608 toward the end 606. Moreover, as shown in FIG. 19, interior projections 648 are integral with, and made of the same material as, the crimp 600.

The wall of the crimp may include anywhere from zero to many openings as desired for the intended purpose. Such openings may be configured in a variety of ways, such as illustrated in FIGS. 14 and 15.

The slit formed by the longitudinal edges of the crimp may be linear, such as shown in FIG. 3, or non-linear. For example only, the edges of the slit may be curved (similar to a sine wave) or otherwise configured to interlock and inhibit translational movement of one edge relative to another edge. This has the advantage of better maintaining the form of the crimp during its insertion into the bone tunnel.

The crimp may be configured as a unitary body without a slit. An example is shown in FIG. 15 with sleeve 400. As another example, crimp 600 shown in FIGS. 19 and 20 may be formed as a unitary body without a slit. The free end of the tendon may be compressed into the interior of the crimp with the push-rod. The flexible interior spines would then act to retain the free end of the tendon within the crimp. The crimp may then be left in the bone opening after withdrawing the push-rod. The crimp may be formed of a rubber material or a biomaterial as described above, and may have one or more openings through which the tendon may integrate with the bone.

The crimp and associated methods may be configured for only partial insertion into a bone structure. For example only, a surgeon may form an opening in a bone that is not a tunnel or through-hole, then insert the crimp into the opening such as shown in FIG. 20. If the crimp is formed from a biomaterial, the tendon will naturally integrate with the bone over time. By not forming a tunnel, more bone is preserved, speeding recovery of the patient.

If desired, the crimp and/or insertion shield may be combined with a material adapted to facilitate growth and integration between the tendon and bone. Examples of such materials would be apparent to those of ordinary skill in the art.

While various embodiments of the present invention have been described in relation to a crimp, it will be appreciated that the body of the device may be configured so that no crimping is necessary. Examples of such devices include a unitary body without a slit, such as described above, and/or devices formed from a shape memory material such as nitinol, which expands or contracts dependent upon a pre-set temperature.

The features described with respect to one embodiment may be applied to other embodiments, or combined with or interchanged with the features of other embodiments, as appropriate, without departing from the scope of the present invention.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A surgical kit for attaching a tendon or a ligament to bone, comprising:
    a crimp and an insertion shield, said crimp having a first end and an opposite second end, and said insertion shield having a leading end and an opposite trailing end, said second end of said crimp being proximate said trailing end of said insertion shield;
    said crimp being composed of a surgical grade material, said crimp having a sleeve, said sleeve having a length, a central longitudinal axis parallel to the length of said sleeve, an interior surface, an exterior surface, a first cross-section perpendicular to the central longitudinal axis of said sleeve, and a second cross-section perpendicular to the central longitudinal axis of said sleeve, the first and second cross-sections spaced apart from one another along the length of said sleeve, said interior and exterior surfaces of said sleeve each having a plurality of surface projections, said interior surface of said sleeve defining a hollow passage and a first open end into said hollow passage, said hollow passage being coaxial with the central longitudinal axis, said first open end being formed at said first end of said crimp, said first open end being configured to pass at least an end of the tendon or ligament therethrough and into said hollow passage of said sleeve, said sleeve being compressible along substantially the entire length thereof to compress the at least the end of the tendon or ligament inserted into said hollow passage, the areas of the first and second cross-sections being greater when said sleeve is uncompressed than when said sleeve is compressed; and
    said insertion shield being configured to facilitate insertion of said crimp into an opening in the bone, said insertion shield having a length from said leading end to said trailing end, a central longitudinal axis parallel to the length of said insertion shield, a third cross-section perpendicular to the central longitudinal axis of said insertion shield and adjacent said trailing end thereof, a fourth cross-section perpendicular to the central longitudinal axis of said insertion shield and between said leading and trailing ends thereof, and a fifth cross-section perpendicular to the central longitudinal axis of said insertion shield and adjacent said leading end thereof, the areas of said third cross-section, said fourth cross-section, and said fifth cross-section decreasing from said trailing end to said leading end.

2. The kit of claim 1, further comprising a suture configured for pulling said crimp, said insertion shield, and the tendon or the ligament through the opening in the bone.

3. The kit of claim 1, wherein said surface projections of said exterior surface of said crimp are configured to facilitate insertion of said crimp through the opening, and resist expulsion of said crimp in a direction opposite to the direction of insertion.

4. The kit of claim 1, wherein said surface projections of said exterior surface include ratchetings.

5. The kit of claim 1, wherein said insertion shield between said fourth and fifth cross-sections is frusto-conical.

6. The kit of claim 1, wherein said interior surface defines a second open end into said hollow passage, said second open end being formed at said second end of said crimp, said second open end being configured to pass the at least end of the tendon or ligament therethrough.

7. The kit of claim 1, wherein said exterior surface has a pair of edges along the length of said sleeve, said pair of edges being substantially parallel with the central longitudinal axis of said sleeve, said pair of edges defining a slot, said slot having a distance between said pair of edges, wherein said distance is adapted to be reduced when said sleeve is compressed.

8. The kit of claim 1, wherein said surface projections on said exterior surface are flexible, generally arcuate, and extend in a direction from said second end of said sleeve toward said first end of said sleeve.

9. The kit of claim 1, wherein said surface projections on said exterior surface are integral with and made of the same surgical grade material as said crimp.

10. The kit of claim 1, wherein said surface projections on said interior surface are flexible, generally diagonal, and extend in a direction from said first end of said sleeve toward said second end of said sleeve.

11. The kit of claim 1, wherein said surface projections on said interior surface are integral with and made of the same surgical grade material as said crimp.

12. The kit of claim 1, wherein said surface projections on said exterior surface are flexible, generally arcuate, and extend in a direction from said second end of said sleeve toward said first end of said sleeve, said surface projections on said interior surface are flexible, generally diagonal, and extend in a direction from said first end of said sleeve toward said second end of said sleeve, and lengths of said surface projections on said exterior surface are different from lengths of said surface projections on said interior surface.

13. The kit of claim 12, wherein said surface projections on said exterior surface are adapted to facilitate insertion of said crimp into the opening in the bone, while resisting expulsion of said crimp therefrom, and said surface projections on said interior surface are adapted to facilitate insertion of the at least the end of the tendon or ligament into the sleeve, while resisting expulsion of the tendon or ligament therefrom.

14. The kit of claim 13, wherein the length of said surface projections on said exterior surface are greater than the length of surface projections on said interior surface.

* * * * *